US012559444B2

(12) United States Patent
    Ihara et al.

(10) Patent No.:  US 12,559,444 B2
(45) Date of Patent:      Feb. 24, 2026

(54) TREATMENT APPARATUS AND TREATMENT METHOD FOR RAW MATERIAL

(71) Applicant: EBARA ENVIRONMENTAL PLANT CO., LTD., Tokyo (JP)

(72) Inventors: Takayuki Ihara, Tokyo (JP); Takashi Fujiwara, Tokyo (JP); Norihisa Miyoshi, Tokyo (JP)

(73) Assignee: EBARA ENVIRONMENTAL PLANT CO., LTD., Tokyo (JP)

( * ) Notice: Subject to any disclaimer, the term of this patent is extended or adjusted under 35 U.S.C. 154(b) by 752 days.

(21) Appl. No.: 17/801,593

(22) PCT Filed: Dec. 8, 2020

(86) PCT No.: PCT/JP2020/045676
    § 371 (c)(1),
    (2) Date: Aug. 23, 2022

(87) PCT Pub. No.: WO2021/171731
    PCT Pub. Date: Sep. 2, 2021

(65) Prior Publication Data
    US 2023/0081521 A1      Mar. 16, 2023

(30) Foreign Application Priority Data

Feb. 28, 2020    (JP) ................................. 2020-033408

(51) Int. Cl.
    *C07C 1/12*            (2006.01)
    *C25B 1/04*            (2021.01)
    (Continued)

(52) U.S. Cl.
    CPC .................. *C07C 1/12* (2013.01); *C25B 1/04* (2013.01); *C25B 9/70* (2021.01); *F23G 5/027* (2013.01);
    (Continued)

(58) Field of Classification Search
    CPC .... C07C 1/12; C07C 9/04; C25B 1/04; C25B 9/70; C25B 15/081; C25B 9/00;
    (Continued)

(56) References Cited

U.S. PATENT DOCUMENTS 3,853,498 A * 12/1974 Bailie ........................ C10J 3/58
                                                        201/31
2006/0137579 A1    6/2006  Fujimura et al.
                    (Continued)

FOREIGN PATENT DOCUMENTS

CN          100363461 C      1/2008
DE       102016110498 A1      4/2024
                    (Continued)

OTHER PUBLICATIONS

European Patent Office, Extended European Search Report in European Patent Application No. 20921253.9, 6 pp. (Jul. 17, 2023).
                    (Continued)

*Primary Examiner* — David J Laux
(74) *Attorney, Agent, or Firm* — Leydig, Voit & Mayer, Ltd.

(57)              ABSTRACT

The present invention relates to a technique for treating a raw material, such as combustible waste, and more particularly to combustion, and pyrolysis and gasification treatment techniques that does not emit carbon dioxide into the atmosphere. A treatment apparatus includes a fluidized-bed furnace having a pyrolysis chamber and a combustion chamber therein, the pyrolysis chamber and the combustion chamber are separated by a partition wall, an electrolysis device configured to electrolyze water to generate hydrogen and oxygen, a methanation reactor configured to produce methane from carbon dioxide discharged from the combustion chamber and the hydrogen, a first fluidizing-gas supply line configured to supply a first fluidizing gas to the pyrolysis (Continued)

chamber, and a second fluidizing-gas supply line configured to introduce a second fluidizing gas to the combustion chamber, the second fluidizing gas including the oxygen and a part of the carbon dioxide.

5 Claims, 3 Drawing Sheets

(51) Int. Cl.
  *C25B 9/70*     (2021.01)
  *F23G 5/027*    (2006.01)
  *F23G 5/30*     (2006.01)
  *F23G 5/44*     (2006.01)
(52) U.S. Cl.
  CPC ................. *F23G 5/30* (2013.01); *F23G 5/44* (2013.01); *F23G 2200/00* (2013.01)
(58) Field of Classification Search
  CPC ... F23G 5/027; F23G 5/30; F23G 5/44; F23G 2200/00; F23G 5/46; C10L 2290/02; C10L 2290/38; C10L 3/08; C10B 51/00; C10B 53/00; C10B 53/02; Y02E 60/36; F23J 15/022; F23J 15/00; C07B 61/00
  See application file for complete search history.

(56)                References Cited

U.S. PATENT DOCUMENTS

| | | | |
|---|---|---|---|
| 2016/0257897 A1* | 9/2016 | Kara | ........................ C10J 3/84 |
| 2019/0024002 A1 | 1/2019 | Bak | |
| 2020/0208274 A1* | 7/2020 | Gorse | ................ F02D 19/0671 |

FOREIGN PATENT DOCUMENTS

| | | | |
|---|---|---|---|
| JP | H10-185170 | A | 7/1998 |
| JP | 2001-192877 | A | 7/2001 |
| JP | 2007-528974 | A | 10/2007 |
| JP | 2008-002725 | A | 1/2008 |
| JP | 2017-089916 | A | 5/2017 |
| JP | 2018-165388 | A | 10/2018 |
| JP | 2019-037121 | A | 3/2019 |
| WO | WO 2001/038788 | A1 | 5/2001 |

OTHER PUBLICATIONS

Japanese Patent Office, International Search Report in International Patent Application No. PCT/JP2020/045676 (Jan. 26, 2021).

* cited by examiner

TREATMENT APPARATUS AND TREATMENT METHOD FOR RAW MATERIAL

TECHNICAL FIELD

The present invention relates to a technique for treating a raw material, such as combustible waste, and more particularly to combustion, pyrolysis, and gasification treatment techniques that do not emit carbon dioxide into the atmosphere.

BACKGROUND ART

Since carbon dioxide ($CO_2$) may be cause of global warming, it is required to reduce an amount of emission of the carbon dioxide. However, various combustion apparatuses, such as waste treatment systems, inevitably generate the carbon dioxide when combustible materials are combusted. Therefore, it has become an important issue to reduce the amount of emission of the carbon dioxide into the atmosphere.

On the other hand, an attempt has been made to recover the carbon dioxide discharged from the combustion apparatus and store the carbon dioxide in the ground, etc. However, in order to recover high-concentration carbon dioxide, it is necessary to completely combust a combustion exhaust gas containing the carbon dioxide discharged from the combustion apparatus with oxygen, or to separate the carbon dioxide from the combustion exhaust gas. Such a treatment cycle may require additional equipment and may increase costs.

CITATION LIST

Patent Literature

Patent document 1: Japanese laid-open patent publication No. 2018-165388

SUMMARY OF INVENTION

Technical Problem

Therefore, the present invention provides a treatment apparatus and a treatment method capable of theoretically reducing an amount of carbon dioxide emitted into the atmosphere to zero and capable of contributing to prevention of global warming.

Solution to Problem

In an embodiment, there is provided a treatment apparatus for a raw material, comprising: a fluidized-bed furnace having a pyrolysis chamber and a combustion chamber therein, the pyrolysis chamber and the combustion chamber being separated by a partition wall; an electrolysis device configured to electrolyze water to generate hydrogen and oxygen; a methanation reactor configured to produce methane from carbon dioxide discharged from the combustion chamber and the hydrogen; a first fluidizing-gas supply line configured to supply a first fluidizing gas to the pyrolysis chamber; and a second fluidizing-gas supply line configured to introduce a second fluidizing gas to the combustion chamber, the second fluidizing gas including the oxygen and a part of the carbon dioxide.

In an embodiment, the electrolysis device is electrically connected to a $CO_2$-free power generator.

In an embodiment, the first fluidizing-gas supply line comprises an oxygen-free-gas supply line configured to supply oxygen-free gas as the first fluidizing gas into the pyrolysis chamber.

In an embodiment, the treatment apparatus further comprises a hydrogen holder configured to store the hydrogen generated by the electrolysis device, wherein the hydrogen holder is arranged between the electrolysis device and the methanation reactor.

In an embodiment, the treatment apparatus further comprises an oxygen holder configured to store the oxygen generated by the electrolysis device, wherein the oxygen holder is arranged between the electrolysis device and the combustion chamber.

In an embodiment, there is provided a method of treating a raw material using a fluidized-bed furnace having a pyrolysis chamber and a combustion chamber therein, the pyrolysis chamber and the combustion chamber being partitioned by a partition wall, said method comprising: electrolyzing water to generate hydrogen and oxygen; supplying a first fluidizing gas to the pyrolysis chamber, while moving a fluidized medium in the combustion chamber to the pyrolysis chamber; pyrolyzing the raw material in the pyrolysis chamber; combusting a residue of the raw material in the combustion chamber; producing methane from carbon dioxide discharged from the combustion chamber and the hydrogen; and supplying a second fluidizing gas to the combustion chamber, the second fluidizing gas including the oxygen and a part of the carbon dioxide.

In an embodiment, the electrolysis of the water is performed using $CO_2$-free electric power.

In an embodiment, the first fluidizing gas is an oxygen-free gas.

Advantageous Effects of Invention

According to the present invention, the carbon dioxide discharged from the combustion chamber reacts with the hydrogen generated by the electrolysis device to generate the methane. Therefore, the treatment apparatus and the treatment method according to the present invention can theoretically reduce an amount of the carbon dioxide emitted into the atmosphere to zero.

DESCRIPTION OF EMBODIMENTS

Embodiments of the present invention will now be described with reference to the drawings.

Figure 1:
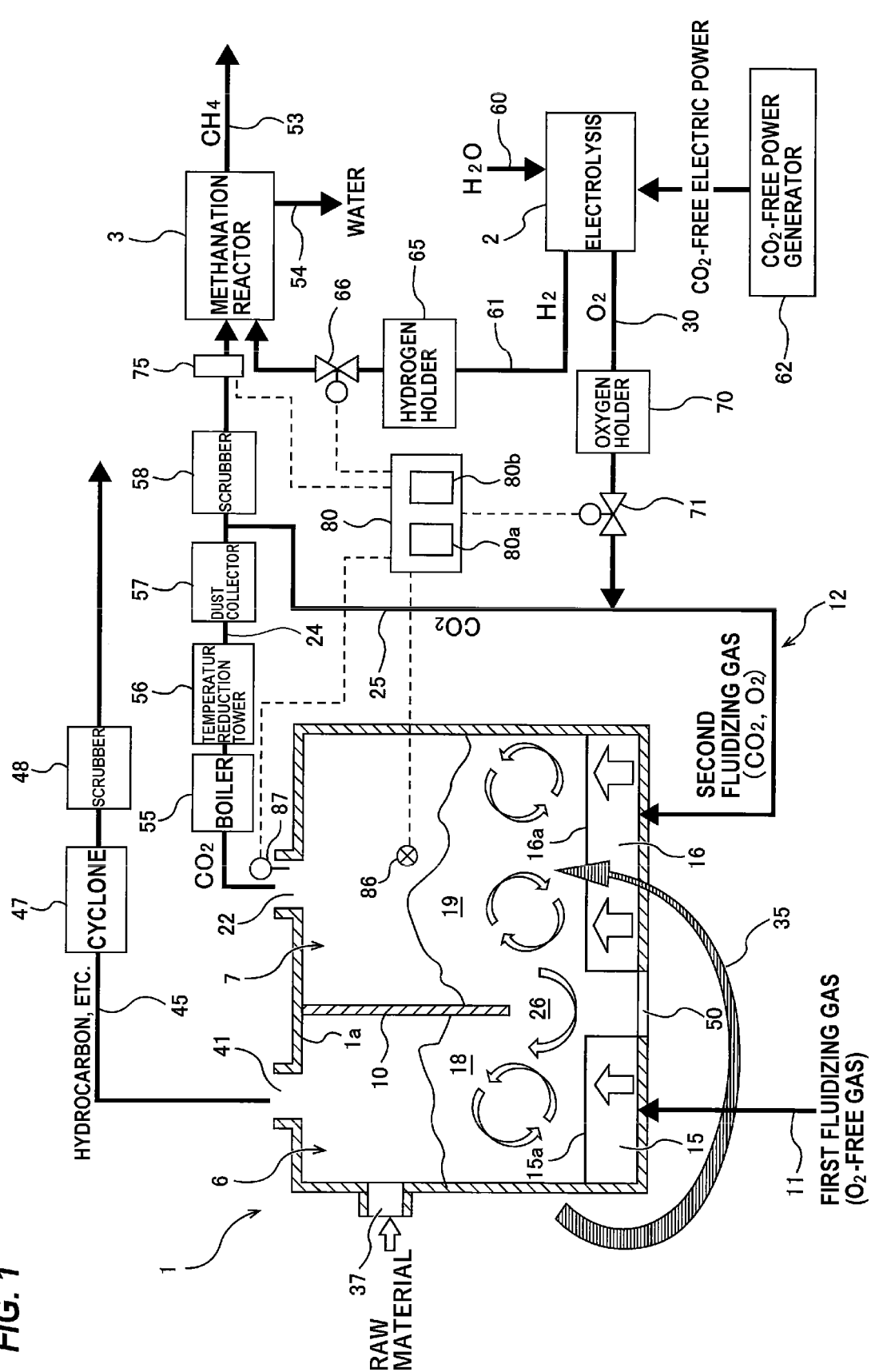
FIG. 1 is a diagram showing an embodiment of a treatment apparatus.

FIG. 1 is a diagram showing an embodiment of a treatment apparatus for treating a raw material, such as combustible waste. The treatment apparatus shown in FIG. 1 includes a fluidized-bed furnace 1 which is an incinerator for the raw material, an electrolysis device 2 configured to electrolyze water to generate hydrogen and oxygen, and a methanation reactor 3 configured to produce methane from carbon dioxide discharged from the fluidized-bed furnace 1 and the hydrogen generated by the electrolysis device 2.

The fluidized-bed furnace 1 includes a pyrolysis chamber 6 configured to pyrolyze the raw material to generate a pyrolysis product, such as hydrocarbon, and a combustion chamber 7 configured to combust a residue of the pyrolyzed raw material. The pyrolysis chamber 6 and the combustion chamber 7 are formed in one fluidized-bed furnace 1. Specifically, the inside of the fluidized-bed furnace 1 is divided into the pyrolysis chamber 6 and the combustion chamber 7 by a partition wall 10. An entire shape of the fluidized-bed furnace 1 is not particularly limited, and the fluidized-bed furnace 1 may have, e.g., a cylindrical shape or a rectangular shape.

A fluidized medium (e.g., silica sand) is contained in the pyrolysis chamber 6 and the combustion chamber 7. In order to fluidize the fluidized medium, the pyrolysis chamber 6 and the combustion chamber 7 are coupled to a first fluid-izing-gas supply line 11 and a second fluidizing-gas supply line 12, respectively.

The first fluidizing-gas supply line 11 is coupled to a first wind box 15 located below the pyrolysis chamber 6, and communicates with the pyrolysis chamber 6 through the first wind box 15. An upper wall of the first wind box 15 is formed of a porous plate 15a. The porous plate 15a consti-tutes a furnace floor of the pyrolysis chamber 6. The first fluidizing-gas supply line 11 supplies a first fluidizing gas into the pyrolysis chamber 6 through the first wind box 15, so that the fluidized medium in the pyrolysis chamber 6 is fluidized. The fluidized medium forms a first fluidized bed 18 in the pyrolysis chamber 6.

The second fluidizing-gas supply line 12 is coupled to a second wind box 16 located below the combustion chamber 7, and communicates with the combustion chamber 7 through the second wind box 16. An upper wall of the second wind box 16 is formed of a porous plate 16a. The porous plate 16a constitutes a furnace floor of the combus-tion chamber 7. The second fluidizing-gas supply line 12 supplies a part of the carbon dioxide discharged from the combustion chamber 7 and the oxygen generated by the electrolysis device 2, both of which serve as a second fluidizing gas, into the combustion chamber 7 through the second wind box 16, so that the fluidized medium in the combustion chamber 7 is fluidized. The fluidized medium forms a second fluidized bed 19 in the combustion chamber 7.

The treatment apparatus includes a combustion-exhaust-gas delivery line 24 extending from an exhaust-gas outlet 22, provided above the combustion chamber 7, to the methana-tion reactor 3. Further, the treatment apparatus includes a carbon-dioxide return line 25 coupled to the combustion-exhaust-gas delivery line 24 and the fluidized-bed furnace 1. End of the carbon-dioxide return line 25 is coupled to the combustion-exhaust-gas delivery line 24, and other end of the carbon-dioxide return line 25 is coupled to the second wind box 16. A part of the carbon dioxide generated in the combustion chamber 7 is returned to the combustion cham-ber 7 through the carbon-dioxide return line 25, and a remaining carbon dioxide is delivered to the methanation reactor 3 through the combustion-exhaust-gas delivery line 24.

The oxygen generated by the electrolysis device 2 is delivered to the combustion chamber 7 through an oxygen delivery line 30 and the carbon-dioxide return line 25. End of the oxygen delivery line 30 is coupled to the electrolysis device 2 and other end of the oxygen delivery line 30 is coupled to the carbon-dioxide return line 25. The oxygen is mixed with the carbon dioxide flowing through the carbon-dioxide return line 25. The mixture of the carbon dioxide and the oxygen flowing through the carbon-dioxide return line 25 is introduced as the second fluidizing gas into the combustion chamber 7, so that the fluidized medium in the combustion chamber 7 is fluidized. In the present embodi-ment, the second fluidizing-gas supply line 12 is constituted of at least a part of the combustion-exhaust-gas delivery line 24, the carbon-dioxide return line 25, and the oxygen delivery line 30.

The partition wall 10 extends downward from an upper wall 1a of the fluidized-bed furnace 1. A lower end of the partition wall 10 is not in contact with the furnace floor, and there is an opening 26 under the partition wall 10. The opening 26 is located at bottoms of the pyrolysis chamber 6 and the combustion chamber 7. The pyrolysis chamber 6 and the combustion chamber 7 communicate with each other through the opening 26. The opening 26 allows the fluidized medium heated in the combustion chamber 7 to move into the pyrolysis chamber 6. The opening 26 is located lower than interfaces (or upper surfaces) of the first fluidized bed 18 and the second fluidized bed 19 in the pyrolysis chamber 6 and the combustion chamber 7.

A swirling flow of the fluidized medium is formed in the combustion chamber 7 by the second fluidizing gas contain-ing the carbon dioxide and the oxygen. The second fluidized bed 19 is formed of such a swirling flow of the fluidized medium. A part of the fluidized medium forming the swirl-ing flow in the combustion chamber 7 flows into the pyroly-sis chamber 6 through the opening 26, and is mixed with the fluidized medium forming the first fluidized bed 18. In the pyrolysis chamber 6, a swirling flow of the fluidized medium is formed by the first fluidizing gas. The first fluidized bed 18 is formed of such a swirling flow of the fluidized medium.

The pyrolysis chamber 6 and the combustion chamber 7 communicate with each other through a communication passage 35. In FIG. 1, an arrow indicating the communica-tion passage 35 is illustrated outside the fluidized-bed fur-nace 1, but the communication passage 35 is located in the fluidized-bed furnace 1. In addition, in FIG. 1, the pyrolysis chamber 6 and the combustion chamber 7 are illustrated in a plane, but the pyrolysis chamber 6 and the combustion chamber 7 actually have a three-dimensional shape. The pyrolysis chamber 6 may be arranged next to the combustion chamber 7. Therefore, the communication passage 35 may be composed of a simple opening.

The fluidized-bed furnace 1 has a raw-material supply port 37 for supplying the raw material, such as waste or biomass, into the pyrolysis chamber 6. The raw material fed into the pyrolysis chamber 6 through the raw-material supply port 37 receives heat from the fluidized medium and is pyrolyzed, while the raw material is agitated by the swirling flow of the fluidized medium forming the first fluidized bed 18. As a result of the pyrolysis, a part of components contained in the raw material form a product gas as a pyrolysis product (e.g., hydrocarbon CnHm, where n and m are integers). The product gas is discharged from the pyrolysis chamber 6 through a product-gas outlet 41 pro-vided on the upper wall 1a of the fluidized-bed furnace 1 constituting the pyrolysis chamber 6. The product-gas outlet 41 communicates with the pyrolysis chamber 6.

A product-gas delivery line 45 is coupled to the product-gas outlet 41. The treatment apparatus includes a cyclone 47 and a scrubber 48 each coupled to the product-gas delivery line 45. The cyclone 47 and the scrubber 48 are arranged in series along the product-gas delivery line 45. The product gas discharged from the pyrolysis chamber 6 is delivered to the cyclone 47 through the product-gas delivery line 45, and dust is removed from the product gas by the cyclone 47. Further, the product gas is delivered to the scrubber 48, and the product gas is cleaned with water (which may be water containing an alkaline agent, such as caustic soda) in the scrubber 48. The scrubber 48 may be configured to clean the product gas with oil instead of the water, or to clean the product gas with water and oil. The product gas purified in this way can be used as a fuel gas, a chemical raw material, etc. In some cases, one or both of the cyclone 47 and the scrubber 48 may not be provided.

In the present embodiment, an oxygen-free gas, which is a gas containing no oxygen, is used as the first fluidizing gas supplied to the pyrolysis chamber 6. Therefore, the first fluidizing-gas supply line 11 of the present embodiment is an oxygen-free-gas supply line. Examples of the oxygen-free gas include a product gas discharged from the pyrolysis chamber 6, water vapor, an inert gas (e.g., nitrogen gas), or methane produced by the methanation reactor 3. The oxygen-free gas may be a mixture of at least two of these product gas, water vapor, inert gas, and methane. In this embodiment, water vapor is used as the first fluidizing gas. The first fluidizing gas may preferably be a combination of the product gas discharged from the pyrolysis chamber 6 and the methane produced by the methanation reactor 3. Since the first fluidizing gas containing the combination of the product gas and methane is a gas having chemical compositions that are close to those of the product gas generated by the pyrolysis of the raw material, a purity of the product gas can be enhanced. If it is desired to contain a chemical substance containing an oxygen atom in the product gas, a gasification reaction may be performed in the pyrolysis chamber 6 by supplying an oxygen-containing gas to an empty tower portion of the pyrolysis chamber 6.

The residue of the raw material in the pyrolysis chamber 6 moves together with the fluidized medium to the combustion chamber 7 through the communication passage 35. The residue of the raw material combusts in the presence of the oxygen contained in the second fluidizing gas, while the residue of the raw material swirls together with the fluidized medium forming the second fluidized bed 19. The residue of the raw material emits thermal energy while generating carbon dioxide with the combustion, and heats the fluidized medium forming the second fluidized bed 19. The carbon dioxide and surplus oxygen are discharged as a combustion exhaust gas from the combustion chamber 7 through the exhaust-gas outlet 22. The exhaust-gas outlet 22 is provided on the upper wall 1a of the fluidized-bed furnace 1 forming the combustion chamber 7. The exhaust-gas outlet 22 communicates with the combustion chamber 7.

A part of the heated fluidized medium flows into the pyrolysis chamber 6 through the opening 26. The heated fluidized medium provides an amount of heat or a calorie required for the pyrolysis of the raw material, whereby pyrolysis of the raw material progresses in the pyrolysis chamber 6. Further, the fluidized medium moves together with the residue of the raw material to the combustion chamber 7 through the communication passage 35. In this way, the fluidized medium circulates between the pyrolysis chamber 6 and the combustion chamber 7.

The raw material to be fed into the pyrolysis chamber 6 is a combustible material containing carbon (C), such as waste plastic, wood, or biomass. The raw material does not combust in the pyrolysis chamber 6, but is pyrolyzed. Since the raw material contains the carbon, carbide (char) is likely to be generated in the pyrolysis chamber 6. The carbide (char) cannot be taken out as a product gas from the pyrolysis chamber 6, but has a large amount of heat. A part of the raw material is discharged as the product gas from the pyrolysis chamber 6, and the residue of the raw material is delivered as the carbide (char) into the combustion chamber 7. This carbide (char) has a large amount of heat or a calorie. Therefore, the carbide (char) generates high thermal energy when the carbide (char) combusts in the combustion chamber 7, and can heat the fluidized medium to a high temperature. A part of the heated fluidized medium moves from the combustion chamber 7 to the pyrolysis chamber 6, and pyrolyzes the raw material.

A incombustible discharge port 50 is provided between the first wind box 15 and the second wind box 16. A relatively large incombustible contained in the raw material is discharged through the incombustible discharge port 50.

The residue of the raw material combusts and generates the carbon dioxide in the combustion chamber 7. The carbon dioxide is discharged from the combustion chamber 7 through the exhaust-gas outlet 22, and is delivered to the methanation reactor 3 through the combustion-exhaust-gas delivery line 24. The methanation reactor 3 has a methanation catalyst (not shown) inside thereof, and causes reaction between the carbon dioxide and hydrogen to produce methane and water ($H_2O$). In this way, the carbon dioxide and hydrogen that have flowed into the methanation reactor 3 are converted into the methane and the water, so that the carbon dioxide is not emitted into the atmosphere. The produced methane is delivered through a methane delivery line 53, and the generated water is discharged from the methanation reactor 3 through a drain 54.

The treatment apparatus includes a boiler 55 coupled to the combustion-exhaust-gas delivery line 24, a temperature reduction tower 56, a dust collector 57, and a scrubber 58. The boiler 55, the temperature reduction tower 56, the dust collector 57, and the scrubber 58 are arranged in series along the combustion-exhaust-gas delivery line 24. A connection point between the carbon-dioxide return line 25 and the combustion-exhaust-gas delivery line 24 is located downstream of the dust collector 57.

The combustion exhaust gas discharged from the combustion chamber 7 is delivered to the boiler 55 through the combustion-exhaust-gas delivery line 24, and waste heat is recovered in the boiler 55. The combustion exhaust gas is delivered to the temperature reduction tower 56 through the combustion-exhaust-gas delivery line 24, and the combustion exhaust gas is cooled in the temperature reduction tower 56. The temperature reduction tower 56 is an example of a cooler for cooling the combustion exhaust gas.

The combustion exhaust gas is further delivered to the dust collector 57 through the combustion-exhaust-gas delivery line 24, and the dust collector 57 removes dust, such as flying ash, from the combustion exhaust gas. The dust collector 57 may be, for example, a bug filter. Further, the combustion exhaust gas is delivered to the scrubber 58 through the combustion-exhaust-gas delivery line 24, and the combustion exhaust gas is cleaned with water (which may be water containing an alkaline chemical, such as caustic soda) in the scrubber 58. The combustion exhaust gas purified in this way is delivered to the methanation reactor 3. At least one of the boiler 55, the temperature reduction tower 56, the dust collector 57, and the scrubber 58 may not be provided. For example, if the heat recovery is not performed, the boiler 55 is not provided.

The electrolysis device 2 is a device configured to electrolyze water into hydrogen and oxygen. The electrolysis device 2 is coupled to a water supply line 60, and the water ($H_2O$) is supplied to the electrolysis device 2 through the water supply line 60. The electrolysis device 2 is further electrically connected to a $CO_2$-free power generator 62. The $CO_2$-free power generator 62 is a power generator driven by renewable energy and does not generate carbon dioxide for power generation. Examples of the renewable energy include solar, wind, hydro, geothermal, solar heat, and biomass (organic matter derived from animals and plants). In the present embodiment, a $CO_2$-free electric power generated by such $CO_2$-free power generator 62 is supplied to the electrolysis device 2. In order to absorb fluctuations in the power generated by the $CO_2$-free power generator 62, the $CO_2$-free electric power generated by the $CO_2$-free power generator 62 may be temporarily stored in a storage battery (not shown), and the storage battery may supply the $CO_2$-free power to the electrolysis device 2.

The electrolysis device 2 electrolyzes the water with the $CO_2$-free electric power to generate hydrogen and oxygen. The hydrogen is delivered to the methanation reactor 3 through a hydrogen delivery line 61. The oxygen is supplied to the combustion chamber 7 through the oxygen delivery line 30 and the carbon-dioxide return line 25. The hydrogen delivery line 61 extends from the electrolysis device 2 to the methanation reactor 3. The oxygen delivery line 30 extends from the electrolysis device 2 to the carbon-dioxide return line 25. In one embodiment, the oxygen delivery line 30 may extend from the electrolysis device 2 to the second wind box 16.

The treatment apparatus includes a hydrogen holder 65 coupled to the hydrogen delivery line 61, a hydrogen flow-rate control valve 66 attached to the hydrogen delivery line 61, an oxygen holder 70 coupled to the oxygen delivery line 30, and an oxygen flow-rate control valve 71 attached to the oxygen delivery line 30. The hydrogen holder 65 is located between the electrolysis device 2 and the methanation reactor 3, and the oxygen holder 70 is located between the electrolysis device 2 and the combustion chamber 7.

The hydrogen generated by the electrolysis device 2 flows through the hydrogen delivery line 61 and is temporarily stored in the hydrogen holder 65. The hydrogen flow-rate control valve 66 is located between the hydrogen holder 65 and the methanation reactor 3. When the hydrogen flow-rate control valve 66 is opened, the hydrogen in the hydrogen holder 65 is delivered to the methanation reactor 3 through the hydrogen delivery line 61 and the hydrogen flow-rate control valve 66. The carbon dioxide and the hydrogen react in the methanation reactor 3 and are converted to the methane and the water ($H_2O$).

An amount of the hydrogen to be delivered to the methanation reactor 3 is such that the total amount of the carbon dioxide in the methanation reactor 3 reacts with the total amount of the hydrogen to produce methane. Thus, in order to deliver the hydrogen to the methanation reactor 3 at an appropriate flow rate, the treatment apparatus includes a carbon-dioxide measuring device 75 configured to measure a flow rate of the carbon dioxide flowing into the methanation reactor 3, and a controller 80 configured to regulate an opening degree of the hydrogen flow-rate control valve 66 based on a measured value of the flow rate of the carbon dioxide. The carbon-dioxide measuring device 75 is attached to the combustion-exhaust-gas delivery line 24 at a position immediately upstream of the methanation reactor 3. The carbon-dioxide measuring device 75 is configured to serve as both a flow meter and a concentration meter. Specifically, the carbon-dioxide measuring device 75 is configured to measure a flow rate of the combustion exhaust gas flowing through the combustion-exhaust-gas delivery line 24, measure a concentration of the carbon dioxide in the combustion exhaust gas, and calculate the flow rate of the carbon dioxide from the flow rate of the combustion exhaust gas and the concentration of carbon dioxide. The carbon-dioxide measuring device 75 is electrically connected to the controller 80, and the measured value of the flow rate of the carbon dioxide is transmitted to the controller 80.

The controller 80 regulates the opening degree of the hydrogen flow-rate control valve 66 based on the flow rate of the carbon dioxide flowing into the methanation reactor 3 (i.e., the measured value of the flow rate of the carbon dioxide transmitted from the carbon-dioxide measuring device 75). The controller 80 is configured to control a flow rate of the hydrogen delivered to the methanation reactor 3. More specifically, when the flow rate of the carbon dioxide increases, the controller 80 operates the hydrogen flow-rate control valve 66 to increase the flow rate of the hydrogen, and when the flow rate of the carbon dioxide decreases, the controller 80 operates the hydrogen flow-rate control valve 66 to reduce the flow rate of the hydrogen. With such control operation of the controller 80, all of the carbon dioxide contained in the combustion exhaust gas can react with the hydrogen to generate the methane. As a result, the amount of carbon dioxide emitted to the outside of the treatment apparatus is theoretically zero. The methane can be used as a fuel gas, such as city gas.

The controller 80 is composed of at least one computer. The controller 80 includes a memory 80a storing programs therein, and an arithmetic device 80b configured to perform arithmetic operations according to instructions contained in the programs. The memory 80a includes a main memory, such as a RAM, and an auxiliary memory, such as a hard disk drive (HDD) or a solid state drive (SSD). Examples of the arithmetic device 80b include a CPU (central processing unit) and a GPU (graphic processing unit). However, the specific configuration of the controller 80 is not limited to this embodiment.

The oxygen generated by the electrolysis device 2 flows through the oxygen delivery line 30 and is temporarily stored in the oxygen holder 70. The oxygen flow-rate control valve 71 is located between the oxygen holder 70 and the carbon-dioxide return line 25. When the oxygen flow-rate control valve 71 is opened, the oxygen in the oxygen holder 70 is delivered to the combustion chamber 7 through the oxygen delivery line 30, the oxygen flow-rate control valve 71, and the carbon-dioxide return line 25. The oxygen is consumed for the combustion of the residue of the raw material in the combustion chamber 7.

The treatment apparatus includes a thermometer 86 disposed in the combustion chamber 7. In the present embodiment, one thermometer 86 is disposed, but a plurality of thermometers 86 arranged along a vertical direction may be provided. The thermometer 86 is electrically connected to the controller 80, and a measured value of temperature in the combustion chamber 7 is transmitted to the controller 80.

The controller 80 is configured to regulate an opening degree of the oxygen flow-rate control valve 71 based on the temperature in the combustion chamber 7 (i.e., the measured value of the temperature in the combustion chamber 7 transmitted from the thermometer 86). More specifically, the controller 80 is configured to regulate the opening degree of the oxygen flow-rate control valve 71 (i.e., a flow rate of the oxygen supplied to the combustion chamber 7) such that the temperature in the combustion chamber 7 is maintained within a predetermined range. In one embodiment, the controller 80 may be configured to regulate the opening degree of the oxygen flow-rate control valve 71 based on an oxygen concentration at the exhaust-gas outlet 22 of the combustion chamber 7 (i.e., a measured value of an oxygen concentration at the exhaust-gas outlet 22 transmitted from an oxygen-concentration measuring device 87). More specifically, the controller 80 is configured to regulate the opening degree of the oxygen flow-rate control valve 71 (i.e., an amount of the oxygen supplied to the combustion chamber 7) such that the oxygen concentration at the exhaust-gas outlet 22 of the combustion chamber 7 is maintained within a predetermined range.

As described above, the part of the carbon dioxide discharged from the combustion chamber 7 is mixed with the oxygen generated by the electrolysis device 2, and returned to the combustion chamber 7. The oxygen acts as an oxidizing agent that oxidizes carbon (C) contained in the residue of the raw material in the combustion chamber 7. An amount of oxygen ($O_2$) in the combustion chamber 7 is slightly larger than an amount of the carbon (C) contained in the residue of the raw material in the combustion chamber 7. The oxygen in the amount larger than such a theoretically optimum amount can absorb fluctuations in the amount of the carbon in the combustion chamber 7, and can prevent generation of carbon monoxide. The carbon in the residue of the raw material reacts with the oxygen to produce the carbon dioxide. The carbon dioxide forms the combustion exhaust gas together with the residual oxygen that is not consumed in the reaction with the carbon, and the combustion exhaust gas is discharged from the combustion chamber 7 through the exhaust-gas outlet 22.

The methanation reaction is represented by the following formula (1), and the electrolysis reaction formula of the water is represented by the following formula (2).

$$CO_2 + 4H_2 \rightarrow CH_4 + 2H_2O \qquad (1)$$

$$2H_2O \rightarrow 2H_2 + O_2 \qquad (2)$$

As can be seen from the above formula (1), four equivalents of $H_2$ are required to convert one equivalent of $CO_2$ to $CH_4$. According to the above formula (2), when four equivalents of $H_2$ are obtained by the electrolysis of the water, two equivalents of $O_2$ are generated.

In the combustion chamber 7 of the fluidized-bed furnace 1, one equivalent of $O_2$ is required to combust one equivalent of carbon (C). Normally, in the combustion process of the waste, a ratio of the oxygen to the carbon is about 1.2 to 1.3, and thus 0.7 to 0.8 equivalents of $O_2$ is surplus. The surplus $O_2$ may be sold as oxygen gas, or may be used as a gas for a melting oxygen burner in a gasification melting furnace facility provided adjacent to the treatment apparatus.

In this embodiment, air is not used as the second fluidizing gas for fluidizing the fluidized medium in the combustion chamber 7. Therefore, the combustion exhaust gas does not contain nitrogen, so that the combustion exhaust gas containing a high concentration of the carbon dioxide can be obtained. In one example, the concentration of the carbon dioxide in the combustion exhaust gas discharged from the combustion chamber 7 is 95% or more. Remaining component in the combustion exhaust gas is substantially oxygen. As described above, according to the present embodiment, the $CO_2$-rich combustion exhaust gas can be obtained. A part of this $CO_2$-rich combustion exhaust gas is returned as the second fluidizing gas to the combustion chamber 7, and the remaining combustion exhaust gas is delivered to the methanation reactor 3.

As described above, the fluidized-bed furnace 1 includes two treatment chambers, i.e., the pyrolysis chamber 6 and the combustion chamber 7. The raw material is not combusted in the pyrolysis chamber 6, and is heated by the high-temperature fluidized medium to be pyrolyzed. As a result, the product gas, such as a high-calorie hydrocarbon, is produced. Since the product gas does not contain the carbon dioxide, the product gas can be obtained in a high yield. The product gas discharged from the pyrolysis chamber 6 is recovered and can be used as a chemical material.

Components that are not easily pyrolyzed are delivered as the residue of the raw material to the combustion chamber 7. The residue of the raw material is combusted in the presence of the oxygen contained in the second fluidizing gas, and generates the carbon dioxide. In this way, since the fluidized-bed furnace 1 including the two treatment chambers, which are the pyrolysis chamber 6 and the combustion chamber 7, is not required to separate the carbon dioxide from the product gas, the treatment apparatus is required no equipment for separating the carbon dioxide, and the treatment apparatus can be made compact as a whole.

Most of the carbon contained in the raw material is separated as the product gas in the pyrolysis chamber 6. Therefore, an amount of the carbon dioxide generated in the combustion chamber 7 is smaller than an amount of the carbon dioxide when all the carbon in the raw material is combusted in the combustion chamber 7. Therefore, the amount of the carbon dioxide to be reacted with the hydrogen in the methanation reactor 3 is not large, and as a result, the methanation reactor 3 can be made compact.

In recent years, a generation cost for renewable electric power has dropped rapidly, and it is expected that fossil fuel consumption for the power generation will be unnecessary in the near future. However, carbon-containing materials, such as wood and plastic, will be needed into the future as materials that support social life, and the materials with deteriorated quality must be treated as waste. The treatment apparatus according to the present embodiment can also suppress the $CO_2$ emission in the process of the treating such biomass and combustible waste (i.e., the $CO_2$-rich combustion exhaust gas obtained from the combustion chamber 7 can be converted into the methane for chemical recycling).

Figure 2:
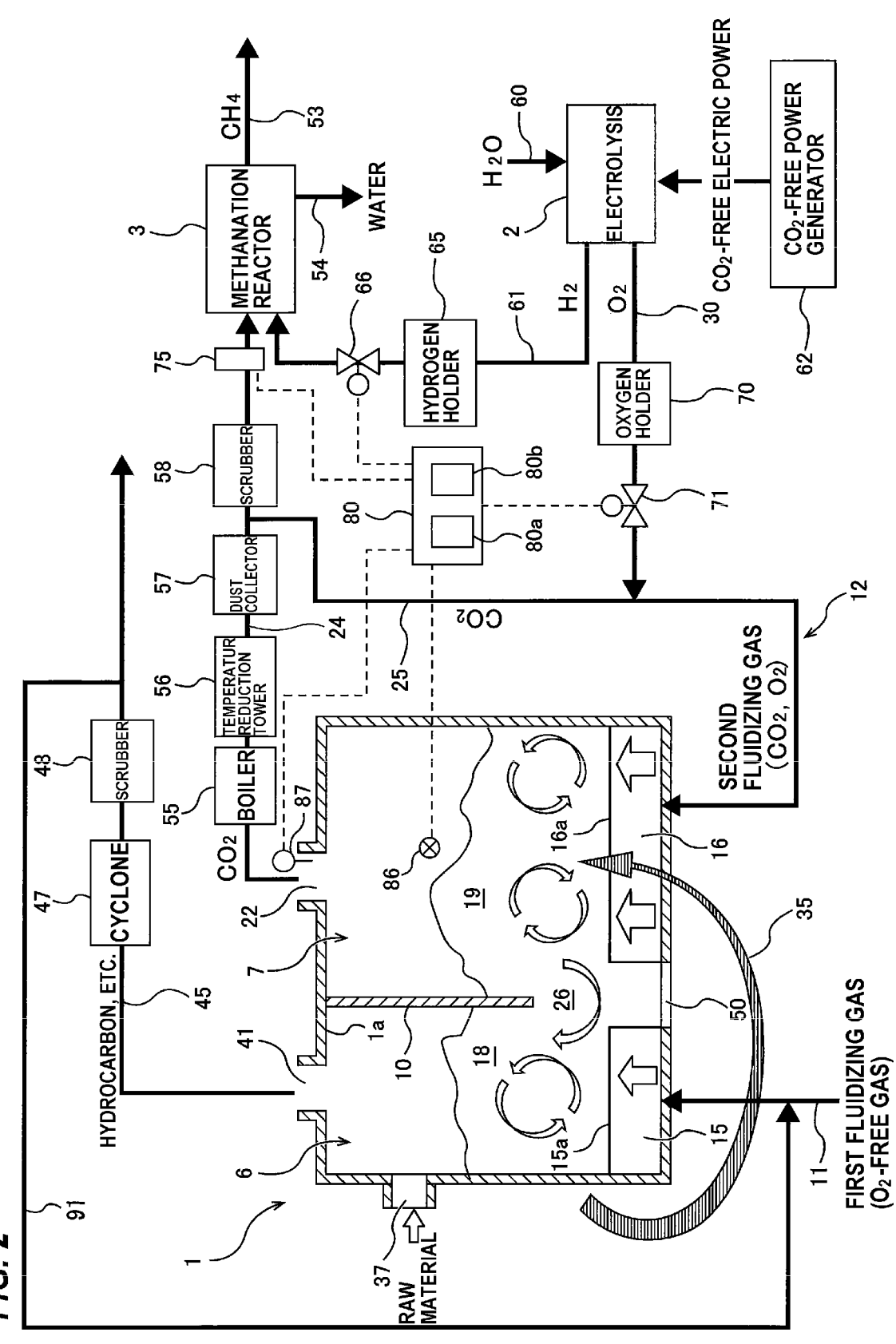
FIG. 2 is a diagram showing another embodiment of the treatment apparatus.

FIG. 2 is a diagram showing another embodiment of the treatment apparatus. Configurations and operations of the present embodiment, which will not be particularly described, are the same as those of the embodiment described with reference to FIG. 1, and duplicated descriptions will be omitted. As shown in FIG. 2, the treatment apparatus includes a product-gas return line 91 extending from the product-gas delivery line 45 to the first fluidizing-gas supply line 11. At least a part of the product gas flowing through the product-gas delivery line 45 is supplied to the first fluidizing-gas supply line 11 through the product-gas return line 91. In the present embodiment, the product gas discharged from the pyrolysis chamber 6 is used as at least a part of the first fluidizing gas which is an oxygen-free gas.

Figure 3:
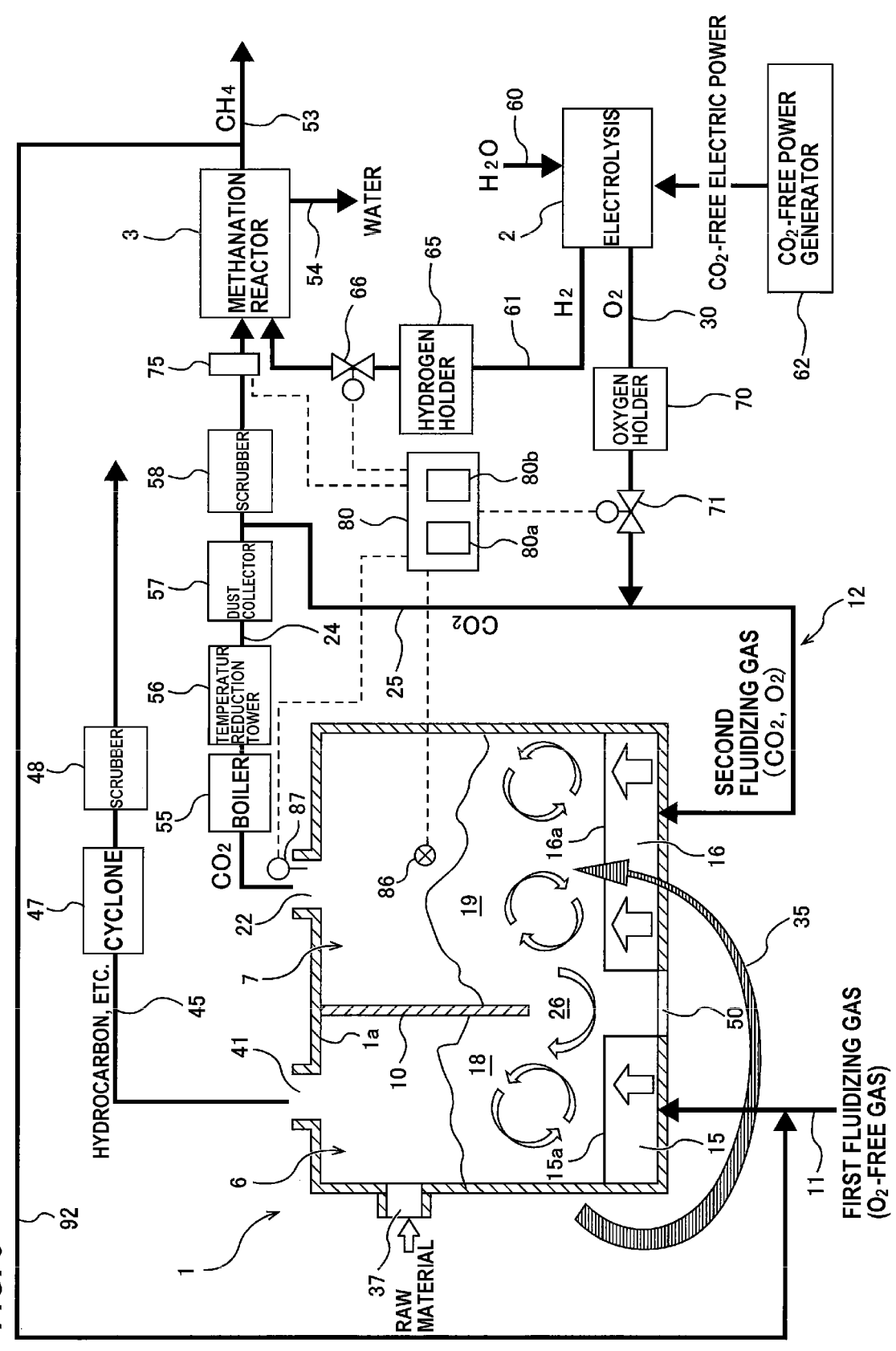
FIG. 3 is a diagram showing still another embodiment of the treatment apparatus.

FIG. 3 is a diagram showing still another embodiment of the treatment apparatus. Configurations and operations of the present embodiment, which will not be particularly described, are the same as those of the embodiment described with reference to FIG. 1, and duplicated descriptions will be omitted. As shown in FIG. 3, the treatment apparatus includes a methane return line 92 extending from the methane delivery line 53 to the first fluidizing-gas supply line 11. At least a part of the methane flowing through the methane delivery line 53 is supplied to the first fluidizing-gas supply line 11 through the methane return line 92. In the present embodiment, the methane discharged from the methanation reactor 3 is used as at least a part of the first fluidizing gas which is an oxygen-free gas.

The above-described techniques of the present invention can be applied not only to a fluidized-bed furnace having a pyrolysis chamber and a combustion chamber therein, but also to an incineration-type fluidized-bed furnace having a combustion chamber but not having a pyrolysis chamber therein. When the present invention is applied to this incineration-type fluidized-bed furnace, the flow of the combustion exhaust gas is in an order of a fluidized-bed furnace, a boiler, a temperature reduction tower, a dust collector, and an induction blower. Normally, the entire amount of combustible components (hydrogen, oxygen, nitrogen, sulfur, chlorine, etc.) in the raw material is combusted with air. Therefore, a combustion exhaust gas contains $N_2$ (nitrogen), $CO_2$, $H_2O$, sulfur oxide, nitrogen oxide, hydrogen chloride, etc. In order to recover only the $CO_2$ from this combustion exhaust gas, $CO_2$ recovery equipment (amine absorption method or $CO_2$ separation membrane method) is provided.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims.

INDUSTRIAL APPLICABILITY

The present invention is applicable to a technique for treating a raw material, such as combustible waste, and more particularly to combustion, pyrolysis, and gasification treatment techniques that do not emit carbon dioxide into the atmosphere.

REFERENCE SIGNS LIST 1 fluidized-bed furnace
2 electrolysis device
3 methanation reactor
6 pyrolysis chamber
7 combustion chamber
10 partition wall
11 first fluidizing-gas supply line
12 second fluidizing-gas supply line
15 first wind box
16 second wind box
18 first fluidized bed
19 second fluidized bed
22 exhaust-gas outlet
24 combustion-exhaust-gas delivery line
25 carbon-dioxide return line
30 oxygen delivery line
35 communication passage
37 raw-material supply port
41 product-gas outlet
45 product-gas delivery line
47 cyclone
48 scrubber
50 incombustible discharge port
53 methane delivery line
54 drain
55 boiler
56 temperature reduction tower
57 dust collector
58 scrubber
60 water supply line 61 hydrogen delivery line
62 $CO_2$-free power generator
65 hydrogen holder
66 hydrogen flow-rate control valve
70 oxygen holder
71 oxygen flow-rate control valve
75 carbon-dioxide measuring device
80 controller
86 thermometer
87 oxygen-concentration measuring device
91 product-gas return line
92 methane return line

The invention claimed is:

1. A treatment apparatus for a raw material, comprising:
a fluidized-bed furnace having a pyrolysis chamber and a combustion chamber therein, the pyrolysis chamber and the combustion chamber being separated by a partition wall inside the fluidized-bed furnace;
an electrolysis device configured to electrolyze water to generate hydrogen and oxygen;
a methanation reactor configured to produce methane from carbon dioxide discharged from the combustion chamber and the hydrogen;
a first fluidizing-gas supply line configured to supply a first fluidizing gas to the pyrolysis chamber; and
a second fluidizing-gas supply line configured to introduce a second fluidizing gas to the combustion chamber, the second fluidizing gas including the oxygen and a part of the carbon dioxide;
a hydrogen holder configured to store the hydrogen generated by the electrolysis device, wherein the hydrogen holder is arranged between the electrolysis device and the methanation reactor;
a hydrogen flow-rate control valve located between the hydrogen holder and the methane reactor;
an oxygen holder configured to store the generated electrolysis device, wherein the oxygen holder is arranged between the electrolysis device and the combustion chamber;
an oxygen flow-rate control valve located between the oxygen holder and the combustion chamber;
a controller configured to regulate an opening degree of the hydrogen flow-rate control valve based on a measured value of the flow rate of the carbon dioxide flowing into the methanation reactor to thereby control a flow rate of the hydrogen delivered to the methanation reactor,
wherein the controller is further configured to regulate opening degree of the oxygen flow-rate control valve and thus a flow rate of the oxygen to the combustion chamber so as to maintain a temperature in the combustion chamber within a predetermined range.

2. The treatment apparatus according to claim 1, wherein the electrolysis device is electrically connected to a $CO_2$-free power generator.

3. The treatment apparatus according to claim 1, wherein the first fluidizing-gas supply line comprises an oxygen-free-gas supply line configured to supply oxygen-free gas as the first fluidizing gas into the pyrolysis chamber.

4. The treatment apparatus according to claim 1 further comprising:
a product-gas delivery line coupled to a product-gas outlet of the pyrolysis chamber; and
a product-gas return line extending from the product-gas delivery line to the first fluidizing-gas supply line.

5. The treatment apparatus according to claim 1 further comprising:

a methane delivery line configured to deliver the methane produced by the methane reactor; and a methane return line extending from the methane delivery line to the first fluidizing-gas supply line.

* * * * *